(12) United States Patent
Kleinberg et al.

(10) Patent No.: US 10,495,774 B2
(45) Date of Patent: Dec. 3, 2019

(54) METHOD FOR ESTIMATING IRREDUCIBLE WATER SATURATION FROM MERCURY INJECTION CAPILLARY PRESSURE

(71) Applicant: SCHLUMBERGER TECHNOLOGY CORPORATION, Sugar Land, TX (US)

(72) Inventors: Robert L. Kleinberg, Cambridge, MA (US); Flavio da Costa Ferreira, Rio de Janeiro (BR); Austin Boyd, Rio de Janeiro (BR); Stacy L. Reeder, Littleton, MA (US); Rodolfo Oliveira, Vitoria (BR); Victoria Baines, Rio de Janeiro (BR); Nadege Bize-Forest, Rio de Janeiro (BR); Andre Bertolini, Rio de Janeiro (BR)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 782 days.

(21) Appl. No.: 14/595,904

(22) Filed: Jan. 13, 2015

(65) Prior Publication Data
US 2015/0198036 A1    Jul. 16, 2015

Related U.S. Application Data

(60) Provisional application No. 61/926,757, filed on Jan. 13, 2014.

(51) Int. Cl.
| | | |
|---|---|---|
| *G01V 3/14* | (2006.01) | |
| *G01N 15/08* | (2006.01) | |
| *G01N 35/00* | (2006.01) | |

(52) U.S. Cl.
CPC ............ *G01V 3/14* (2013.01); *G01N 15/0886* (2013.01); *G01N 2015/0813* (2013.01); *G01N 2035/00881* (2013.01)

(58) Field of Classification Search
CPC ...... E21B 49/008; E21B 49/08; E21B 49/087; G01V 3/14; G01N 15/0886; G01N 2015/0813
See application file for complete search history.

(56) References Cited

U.S. PATENT DOCUMENTS

| | | | | |
|---|---|---|---|---|
| 4,751,646 A | * | 6/1988 | Alger | ...................... E21B 49/02 324/376 |
| 4,903,207 A | * | 2/1990 | Alger | ..................... E21B 49/005 324/376 |

(Continued)

OTHER PUBLICATIONS

Coates et al., A New Characterization of Bulk-Volume Irreducible Using Magnetic Resonance, Jun. 15-18, 1997, SPWLA 38th Annual Logging Symposium, 14 pp. (Year: 1997).*

(Continued)

*Primary Examiner* — Toan M Le

(57) ABSTRACT

Irreducible water saturation of fluid-storing porous reservoir rock is determined using methods that include obtaining a reservoir rock sample from the underground fluid reservoir; performing mercury saturation measurements on the reservoir rock sample for different mercury injection pressure values to obtain mercury saturation values for the different mercury injection pressure values; and estimating the irreducible water saturation ($Sw_{irr}$) from the mercury saturation values and the mercury injection pressure values by correcting for surface films of fluid retained on pore walls of the reservoir rock.

26 Claims, 10 Drawing Sheets

(56) References Cited

U.S. PATENT DOCUMENTS

| | | | | |
|---|---|---|---|---|
| 5,069,065 | A | * | 12/1991 | Sprunt .................. G01N 13/00 73/152.09 |
| 5,621,169 | A | * | 4/1997 | Harris .................. E21B 47/042 702/13 |
| 7,072,809 | B2 | * | 7/2006 | Egermann .............. G01N 15/08 702/12 |
| 8,645,070 | B2 | * | 2/2014 | Hanson .................. E21B 49/00 324/303 |
| 2002/0173915 | A1 | * | 11/2002 | Egermann .............. G01N 15/08 702/12 |
| 2012/0130639 | A1 | * | 5/2012 | Hanson .................. E21B 49/00 702/2 |

OTHER PUBLICATIONS

Purcell, W. R., "Capillary Pressures—Their Measurement Using Mercury and the Calculation of Permeability Therefrom", Petroleum Transactions AIME, presented at the Branch Fall meeting, Dallas Texas, Oct. 4-6, 1948, pp. 39-48.

Radke, C. J. et al., "A Pore Level Scenario for the Development of Mixed Wettability in Oil Reservoirs", SPE-24880-MS, presented at SPE Annual Technical Conference, Washington, DC, Oct. 4-7, 1992, pp. 163-177.

Sabatier, L., "Comparitive Study of Drainage Capillary Pressure Measurments Using Different Techniques and for Different Fluid Systems", Society of Core Analysts, SCA 9424, 1994, pp. 263-273.

Kleinberg, R. L. et al., "Tapered Cutoffs for Magnetic Resonance Bound Water Volume", SPE 38737-MS, presented at the SPE Annual Technical Conference, San Antonio, TX, Oct. 5-8, 1997, pp. 197-202.

Omoregle, Z. S., "Factors Affecting the Equivalency of Different Capillary Pressure Measurement Techniques", SPE Formation Evaluation, SPE-15384-PA, Mar. 1988, pp. 147-155.

Hartmann, D. J. et al.,"Predicting Reservoir System Quality and Performance", AAPG Treatise of Petroleum Geology/Hand book of Petroleum Geology: Exploring for Oil and Gas Traps, 1999, pp. 9-1 to 9-154.

* cited by examiner

METHOD FOR ESTIMATING IRREDUCIBLE WATER SATURATION FROM MERCURY INJECTION CAPILLARY PRESSURE

CROSS-REFERENCE TO RELATED APPLICATIONS

This application claims priority to U.S. Provisional Patent Application No. 61/926,757 filed Jan. 13, 2014, the entire disclosure of which is hereby expressly incorporated by reference herein.

BACKGROUND

An oil-producing well may produce hydrocarbons or a combination of hydrocarbons and water from a hydrocarbon reservoir. Factors that may determine whether pure hydrocarbons or a mixture of hydrocarbons are extracted from the reservoir rock are the porosity of the reservoir rock and the water saturation at the depth where fluid is extracted from the reservoir. Reservoir rock may retain an amount of water that may not be produced. This water, although present, is held in place by capillary forces and will not flow. The irreducible water saturation, $Sw_{irr}$, characterizes this amount of water as a ratio between the volume of non-producible water held by the capillaries of the reservoir rock and the total porous volume of the reservoir rock. If the actual water saturation at the extraction site is above the irreducible water saturation, $Sw_{irr}$, a mixture of hydrocarbons and water may be produced, whereas only hydrocarbons may be produced if the actual water saturation is at $Sw_{irr}$. Accordingly, in the oil industry, the irreducible water saturation, $Sw_{irr}$, is a useful parameter for predicting the productivity of a hydrocarbon-bearing reservoir.

Different methods for estimating $Sw_{irr}$ exist. $Sw_{irr}$ may be estimated from log analysis methods such as, for example, resistivity well logs and nuclear magnetic resonance (NMR) analysis. The industry standard procedure has been to validate these results using saturation height modeling based on special core analysis (SCAL), where the irreducible water saturation, $Sw_{irr}$, of a core sample is determined in the lab. Using the lab-determined irreducible water saturation, $Sw_{irr}$, saturation height modeling can be applied to predict the actual water saturation in the well, depending on the height above the free-water level in the well, where the water saturation reaches 100%. Multiple methods for performing $Sw_{irr}$ analysis on a sample core exist. Commonly used methods include, for example, the Mercury Injection Capillary Pressure (MICP) method and oil-brine and air-brine centrifugation drainage and porous plate methods.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In general, in one aspect, the present disclosure relates to methods for determining irreducible water saturation in a fluid-storing porous reservoir rock of an underground fluid reservoir. The methods include obtaining a reservoir rock sample from the underground fluid reservoir and performing mercury saturation measurements on the reservoir rock sample for different mercury injection pressure values to obtain mercury saturation values for the different mercury injection pressure values. The methods further include estimating an irreducible water saturation ($Sw_{irr}$) from the mercury saturation values and the different mercury injection pressure values by correcting for surface films of fluid retained on pore walls of the reservoir rock.

In general, in one aspect, the present disclosure relates to a system that includes a processor, memory, and software. The software includes instructions, which when executed by the processor enable the system to perform a method. The method includes estimating an irreducible water saturation ($Sw_{irr}$) from mercury saturation values obtained by performing mercury saturation measurements on a reservoir rock sample for different mercury injection pressure values, and by correcting for surface films of fluid retained on pore walls of the reservoir rock.

In general, in one aspect, the present disclosure relates to a non-transitory computer readable medium comprising instructions that enable a system to perform a method for estimating an irreducible water saturation ($Sw_{irr}$) from mercury saturation values obtained by performing mercury saturation measurements on a reservoir rock sample for different mercury injection pressure values, and by correcting for surface films of fluid retained on pore walls of the reservoir rock.

Other aspects of the disclosure will be apparent from the following description and the appended claims.

BRIEF DESCRIPTION OF DRAWINGS

The subject disclosure is further described in the detailed description which follows, in reference to the noted plurality of drawings by way of non-limiting examples of the subject disclosure, in which like reference numerals represent similar parts throughout the several views of drawings, and wherein.

DETAILED DESCRIPTION

This subject disclosure relates to estimating the irreducible water saturation, $Sw_{irr}$, from capillary pressure curves obtained using mercury injection methods such as, for example, the Mercury Injection Capillary Pressure (MICP) method. Using an MICP method in accordance with one or more embodiments of the present disclosure, it was found by the present inventors that depending on the characteristics of the reservoir rock analyzed, uncorrected MICP analysis data may underestimate $Sw_{irr}$. The uncorrected data obtained using an MICP method in accordance with one or more embodiments of the present disclosure may indicate a $Sw_{irr}$ lower than centrifugation drainage and porous plate methods. It was found that the results obtained using centrifugation drainage and porous plate methods are in better agreement with log-derived estimates of $Sw_{irr}$ than the uncorrected results obtained using MICP analysis. Methods in accordance with one or more embodiments of the present disclosure provide for correction of the data obtained using MICP methods, thus enabling the derivation of accurate $Sw_{irr}$ estimates from MICP method-based data. The particulars shown herein are by way of example and for purposes of illustrative discussion of the subject disclosure only and are presented in the cause of providing what is believed to be the most useful and readily understood description of the principles and conceptual aspects of the subject disclosure. In this regard, no attempt is made to show structural details in more detail than is necessary, the description taken with the drawings making apparent to those skilled in the art how the several forms of the subject disclosure may be embodied in practice. Furthermore, like reference numbers and designations in the various drawings indicate like elements.

Figure 1:
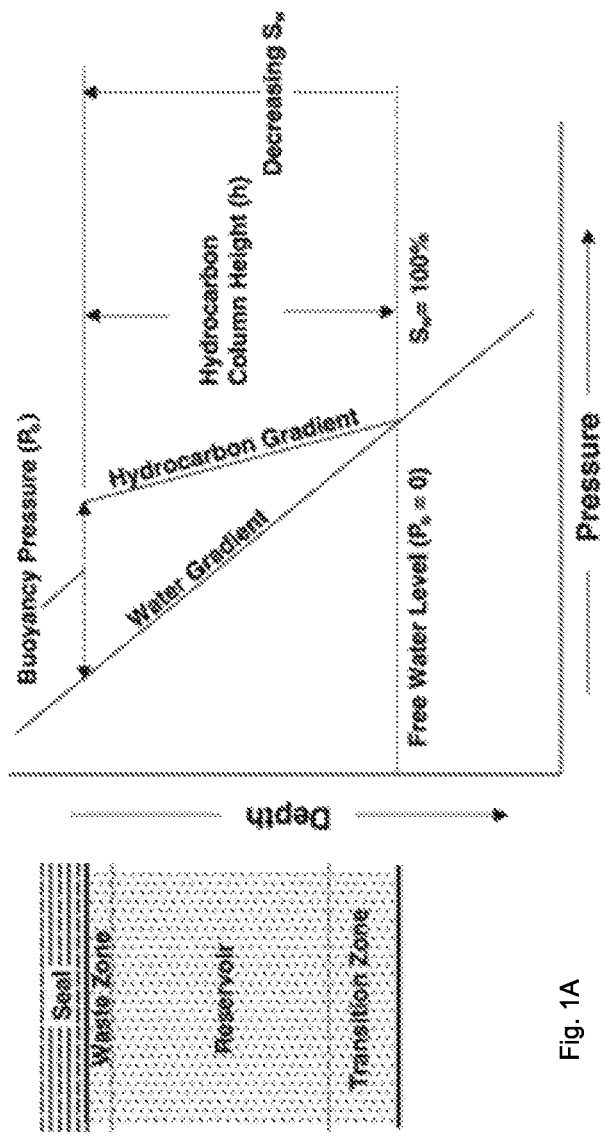
FIGS. 1A and 1B respectively show a sample hydrocarbon reservoir and the associated water and hydrocarbon gradients in accordance with one or more embodiments of the present disclosure.

Hydrocarbons, such as crude oil and natural gas, may be found in certain layers of rock beneath the surface of the earth. Porous and permeable rock may contain hydrocarbons and associated fluids thus forming a reservoir. The associated fluids may be, for example, water or brine. Most oil and gas reservoirs are water wet, i.e. water coats the surface of the reservoir rock. FIG. 1A shows a reservoir model. The bottom of the model is provided by the free water level. At free water level and below, the reservoir rock is 100% saturated with water. In a hypothetical fluid system purely governed by gravity, the free water level is where non-miscible fluids such as oil and water would separate, with water having a higher density accumulating below the free water level, and oil having a lower density accumulating above the free water level. Such a hypothetical fluid system may be, for example, a large open hole drilled through the oil column, where only gravity and buoyancy forces control the fluid distribution in the borehole. The pressure that pushes water downward, i.e. the buoyancy pressure, $P_b$, is proportional to the difference between the densities of water and oil, and may be determined according to Equation 1 shown below:

$$P_b = gh(\rho_w - \rho_o), \quad (1)$$

where g is the gravitation constant; h is the height of the hydrocarbon column above the free water level; $\rho_w$ is the water or brine density; and where $\rho_o$ is the hydrocarbon (oil) density. As shown in FIG. 1B, the pressure exerted on water is proportional to the height of the hydrocarbon column, h.

However, because the hydrocarbons and associated fluids may be stored in capillaries of porous rock, a capillary pressure, $P_c$, causes water to rise within the capillaries of the porous rock until an equilibrium between the capillary pressure, $P_c$, and the buoyancy pressure, $P_b$, is reached. The capillary pressure, $P_c$, may be determined according to Equation 2 shown below:

$$P_c = \frac{2\sigma \cos\theta}{R}, \quad (2)$$

where $\sigma$ is the interfacial tension; $\theta$ is the contact angle; and R is the capillary radius. Values for $\sigma$ and $\theta$ of many liquid/liquid and liquid/gas pairings may be obtained from published tables similar to, for example, Table 1 shown below, or they may be determined experimentally.

TABLE 1

Interfacial tension (IFT), $\sigma$, and contact angle, $\theta$, for common fluid systems.

| System | IFT($\sigma$) | | Theta | Cos($\theta$) | IFT*Cos($\theta$) |
|---|---|---|---|---|---|
| Hg/air | 485 | dynes/cm | 130 | 0.643 | 312 |
| gas/brine | 72 | dynes/cm | 0 | 1.000 | 72 |
| gas/oil | 24 | dynes/cm | 0 | 1.000 | 24 |
| oil/brine | 32 | dynes/cm | 30 | 0.866 | 28 |

Accordingly, a mixture of water and hydrocarbons may exist above the free water level. Because the capillary pressure, $P_c$, is inversely proportional to the capillary radius, R, the level to which water rises may depend on the size of the pores in the reservoir rock. Water may rise furthest in small pores. Accordingly, the distribution of water and hydrocarbons in reservoir rock may depend on the distribution of pore sizes. The distribution of water and hydrocarbons in the pores of the reservoir rock may be characterized by a saturation value for water, Sw. At free water level and below, the water saturation, Sw is 100%. In the transition zone above the free water level, shown in FIG. 1A, Sw gradually decreases, governed by the equilibrium between buoyancy pressure $P_b$ and capillary pressure $P_c$. In a reservoir rock with mostly small pores, the water may rise relatively far, resulting in a wide transition zone, whereas in a reservoir rock with mostly large pores, the water may not rise far above the free water level, resulting in a narrow transition zone. If liquid is extracted from the transition zone, the produced liquid may therefore contain water, i.e. the water cut is non-zero. If liquid is produced from a lower region of the transition zone, the liquid may contain more water, whereas the liquid may contain less water if it is produced from an upper region of the transition zone.

The irreducible water saturation, $Sw_{irr}$, defines the maximum water saturation that a reservoir rock can retain without producing water. This irreducible water, although present, is held in place by capillary forces and may not flow when liquid is extracted. Accordingly, if $Sw \leq Sw_{irr}$, the water cut of a produced liquid may be zero, i.e. the produced liquid may not contain water. In FIG. 1A, the zone where $Sw \leq Sw_{irr}$ is the reservoir zone.

Availability of the $Sw_{irr}$ of the reservoir rock may therefore enable a variety of reservoir interpretations such as, for example, determining the free water level even if below the total depth of the well, height and location of the transition zone, identifying zones that, at least initially, may produce water-free hydrocarbons, and reassessing zones that have been affected by production causing the free water level to rise.

Multiple methods for determining the irreducible water saturation, $Sw_{irr}$, exist. In the reservoir zone, $Sw_{irr}$ may be similar to the water saturation near the well bore. $Sw_{irr}$ may therefore be derived from the water saturation estimated using dielectric logs or using other log data based methods. In accordance with one or more embodiments of the present disclosure, the $Sw_{irr}$ obtained using log data based methods may be validated using laboratory analysis methods such as, for example, saturation height modeling based on special core analysis (SCAL). SCAL methods include, for example, mercury injection capillary pressure (MICP) methods, also known as mercury porosimetry, oil-brine drainage methods, and air-brine drainage by centrifugation or porous plate methods. In accordance with one or more embodiments of the present disclosure, MICP analysis results, obtained under laboratory conditions for a mercury-air fluid combination, may be converted to downhole conditions in order to create a capillary pressure curve to be used for saturation height modeling based on the scenario shown in FIGS. 1A and 1B, and using, for example, Equations 1 and 2. Capillary pressure curves obtained from laboratory analysis and converted to downhole conditions may further be plotted and compared to results obtained using other methods, such as, for example, Archie's equation, thus serving as an aid to evaluate whether a hydrocarbon reservoir is at $Sw_{irr}$ conditions.

Figure 2:
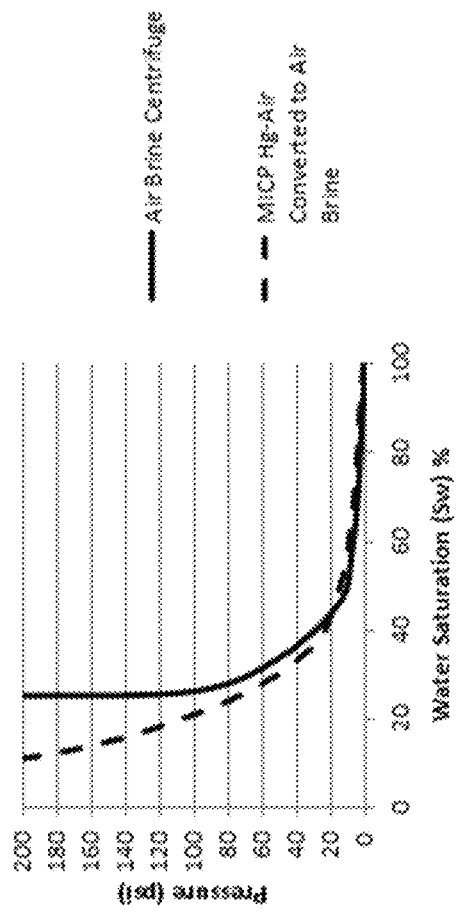
FIG. 2 shows sample capillary pressure curves in accordance with one or more embodiments of the present disclosure.

In accordance with one or more embodiments of the present disclosure, $Sw_{irr}$ estimates may be obtained from a dried reservoir rock sample placed in a chamber of a mercury injection apparatus. The reservoir rock sample may be evacuated, and subsequently, mercury may be injected into the reservoir rock sample using increasingly higher mercury injection pressures. The pressure required for the injection and the volume of mercury injected into the reservoir rock sample may be recorded. A mercury injection pressure curve may be obtained by plotting the mercury injection pressure against the volume of mercury injected. Other methods, such as drainage and centrifugation methods may measure fluid volume extracted from the fluid-saturated reservoir rock. Accordingly, in accordance with one or more embodiments of the present disclosure, conversions may allow to adjust for the experimental procedure used. FIG. 2 shows two capillary pressure curves obtained from a reservoir rock sample. One curve illustrates sample data obtained using an air-brine centrifugation method, whereas the second curve illustrates sample data obtained using the MICP method that have been converted to an air-brine interface.

For high water saturation values and low capillary pressure values, the results of the two methods for obtaining water saturation—capillary pressure relationships for the reservoir rock sample may be in close agreement. However, at reduced water saturation values, the results of the air-brine converted MICP method may consistently indicate a lower water saturation than the results of the air-brine centrifugation method. The air-brine centrifugation results indicate asymptotic behavior of the water saturation at capillary pressures above 100 psi, suggesting an irreducible water saturation, $Sw_{irr}$, of approximately 25%. It has been found that frequently $Sw_{irr}$ results obtained using centrifugation and porous plate analysis methods are in close agreement with $Sw_{irr}$ values obtained from log data. In contrast, the raw MICP data may not show asymptotic behavior in similar pressure ranges, thus making it difficult to determine $Sw_{irr}$ from raw MICP data.

Figure 3:
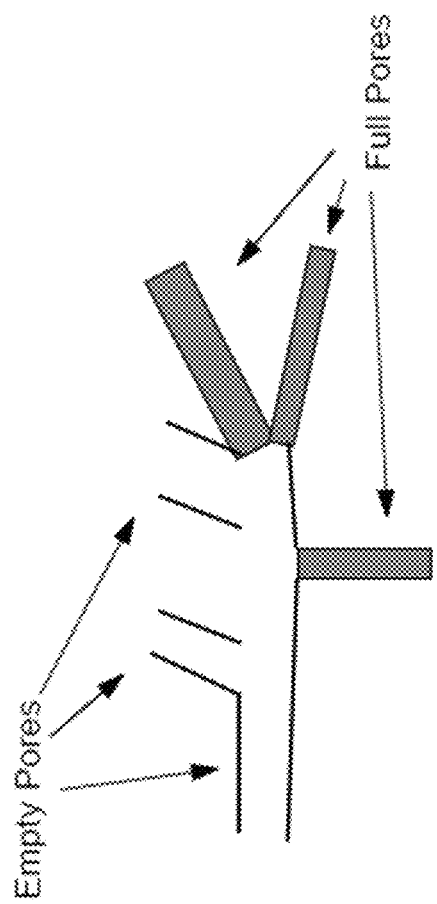
FIG. 3 illustrates an irreducible water saturation model (irreducible water saturation model 1)

The capillary pressure curve obtained using MICP analysis deviates from the capillary pressure curve obtained from centrifugation analysis due to methodological differences. MICP methods are performed on dry rocks. A capillary pressure curve is obtained from observations of the mercury injection pressure necessary to inject a certain volume of mercury into the reservoir rock sample. Such a scenario may be represented by $Sw_{irr}$ model 1, shown in FIG. 3, where an empty pore may be entirely filled with mercury if the injection pressure is sufficient to overcome the capillary pressure opposing the mercury influx. Relatively low mercury injection pressures may be sufficient to overcome the capillary pressure opposing the influx of mercury into large pores. Increasing mercury injection pressures may enable mercury to enter increasingly smaller pores where the capillary pressure opposing the influx of mercury is higher. Assuming an infinite mercury injection pressure, even pores of the smallest size may be filled with mercury.

Figure 4:
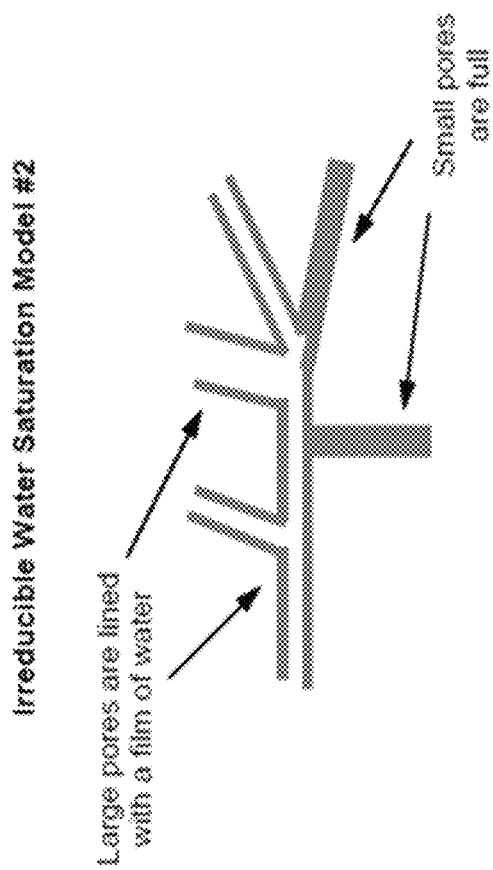
FIG. 4 illustrates an irreducible water saturation model in accordance with one or more embodiments of the present disclosure (irreducible water saturation model 2).

In contrast, centrifugation and porous plate methods are based on withdrawing water from an initially fully water-saturated reservoir rock sample. Residual water, which may be located, for example, in small pores and in thin films lining the walls of larger pores, may not be extracted, and therefore is the irreducible water that determines the irreducible water saturation, $Sw_{irr}$. Accordingly, the asymptotic behavior of the capillary pressure curve obtained from centrifugation or porous plate methods indicates a $Sw_{irr}$ value, where further increases of the capillary pressure do not result in extraction of any additional water from the reservoir rock sample. Such a scenario is properly represented by $Sw_{irr}$ model 2, shown in FIG. 4.

Comparison of model 1 (FIG. 3) and model 2 (FIG. 4) suggests that the discrepancy between capillary pressure curves obtained from MICP analysis and curves obtained from centrifugation or porous plate methods may primarily be a result of the thin fluid films lining the pore walls, thus affecting measurement methods that are based on model 2, i.e. centrifugation and porous plate methods, but not measurement methods that are based on model 1, i.e. MICP methods. Accordingly, $Sw_{irr}$ estimated using MICP methods may be lower than $Sw_{irr}$ estimated using centrifugation and porous plate methods because MCIP methods do not account for the additional water volume of thin fluid films lining the pore walls. Because thin films also may exist under downhole conditions, model 2 may be a more accurate model of irreducible water saturation in reservoir rock under downhole conditions.

In accordance with one or more embodiments of the present disclosure, one method for obtaining $Sw_{irr}$ from measurements that are based on model 1 assumptions, for example MICP measurements, may be to segment the MICP data points based on pore size, and to adjust the data points that fall into pore size ranges where model 1 and model 2 deviate. For example, both models may predict that small pores remain filled with irreducible water, thus assigning 100% of the volume of small pores to irreducible water, i.e. the models agree, and accordingly no correction may be necessary for small pores. For slightly larger pores, model 1 may predict that they drain completely, whereas model 2 may predict that they remain lined with a thin film of water. Accordingly the discrepancy between model 1 and model 2 may be large because model 1 categorizes the slightly larger pore as completely empty (i.e. 0% irreducible water saturation), whereas model 2 predicts that the thin film lining the pore fills almost the entire pore, due to the small diameter of the pore (i.e. a very high degree, although not 100%, of irreducible water saturation). For increasingly larger pore diameters the agreement of the models may improve. Even though model 1 may predict 0% irreducible water saturation, whereas model 2 may predict a thin film of water lining the pore wall, the thin film of water in a pore of a large volume may be negligible. In accordance with one or more embodiments of the present disclosure, data points obtained from a method compatible with model 1 may therefore be transformed to data points compatible with model 2 by adjustments that may be made using weighting factors that form a weighting function. Rather than implementing a sharp cutoff that assigns all pore volume of pores with a radius below a certain threshold to irreducible water, and all pore volume of pores with a radius above the threshold to free water, a weighting function may reassign some pore volume of pores with a radius above the threshold (i.e. pore volume that, according to the mercury injection method, contains free water) to irreducible water, thus correcting for the discrepancy between model 1 and model 2. The weighting function in accordance with one or more embodiments of the present disclosure may implement a graded transition such that almost all pore volume of pores with a radius slightly above the threshold may be assigned to irreducible water, whereas increasingly less pore volume may be assigned to irreducible water for pores of increasing radius. Once this correction has been performed, the irreducible water saturation, obtained for the individual pore sizes, may be summed to obtain the irreducible water saturation $Sw_{irr}$, of the reservoir rock sample.

Figure 7:
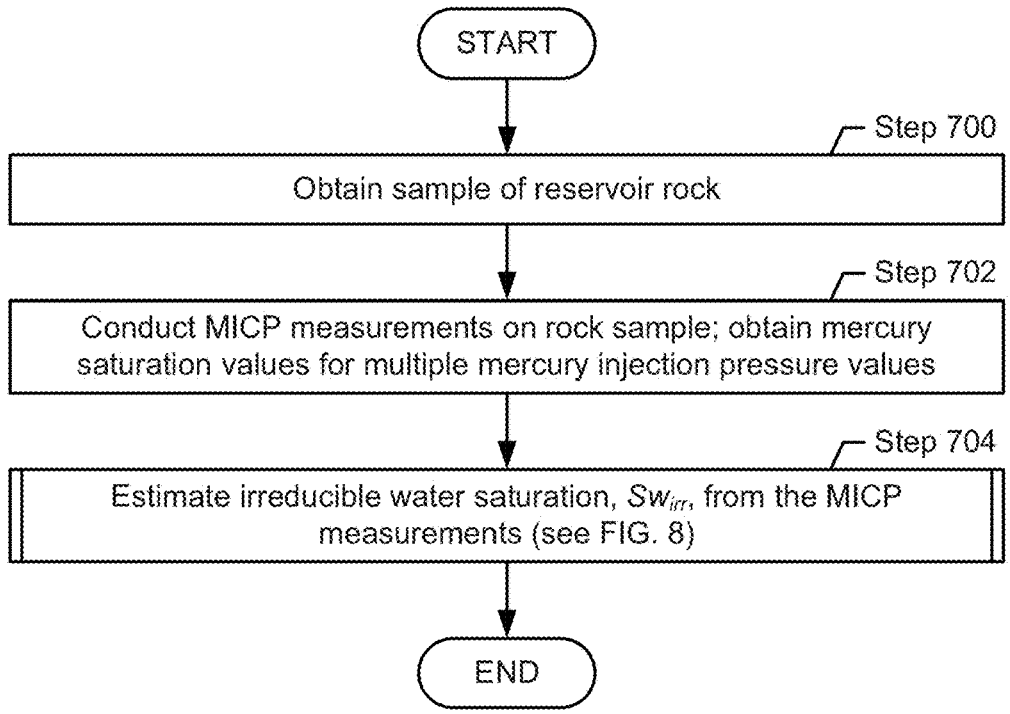
FIGS. 7, 8 and 9 illustrate methods in accordance with one or more embodiments of the present disclosure.
Figure 8:
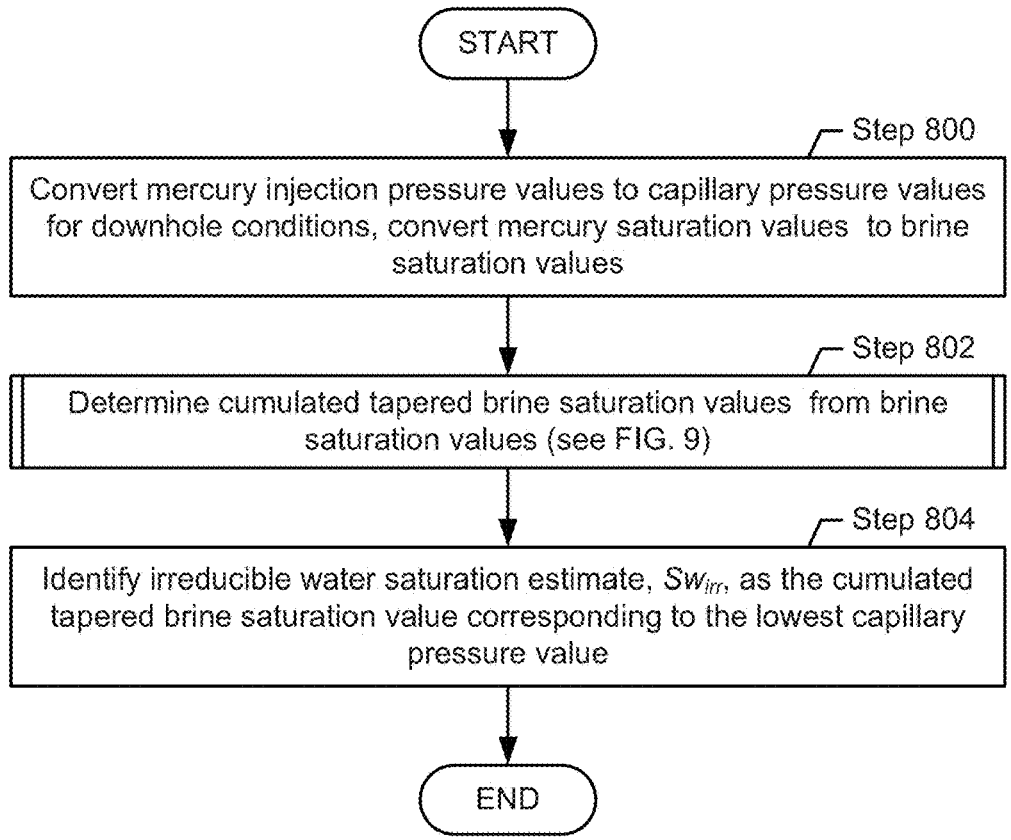
Figure 9:
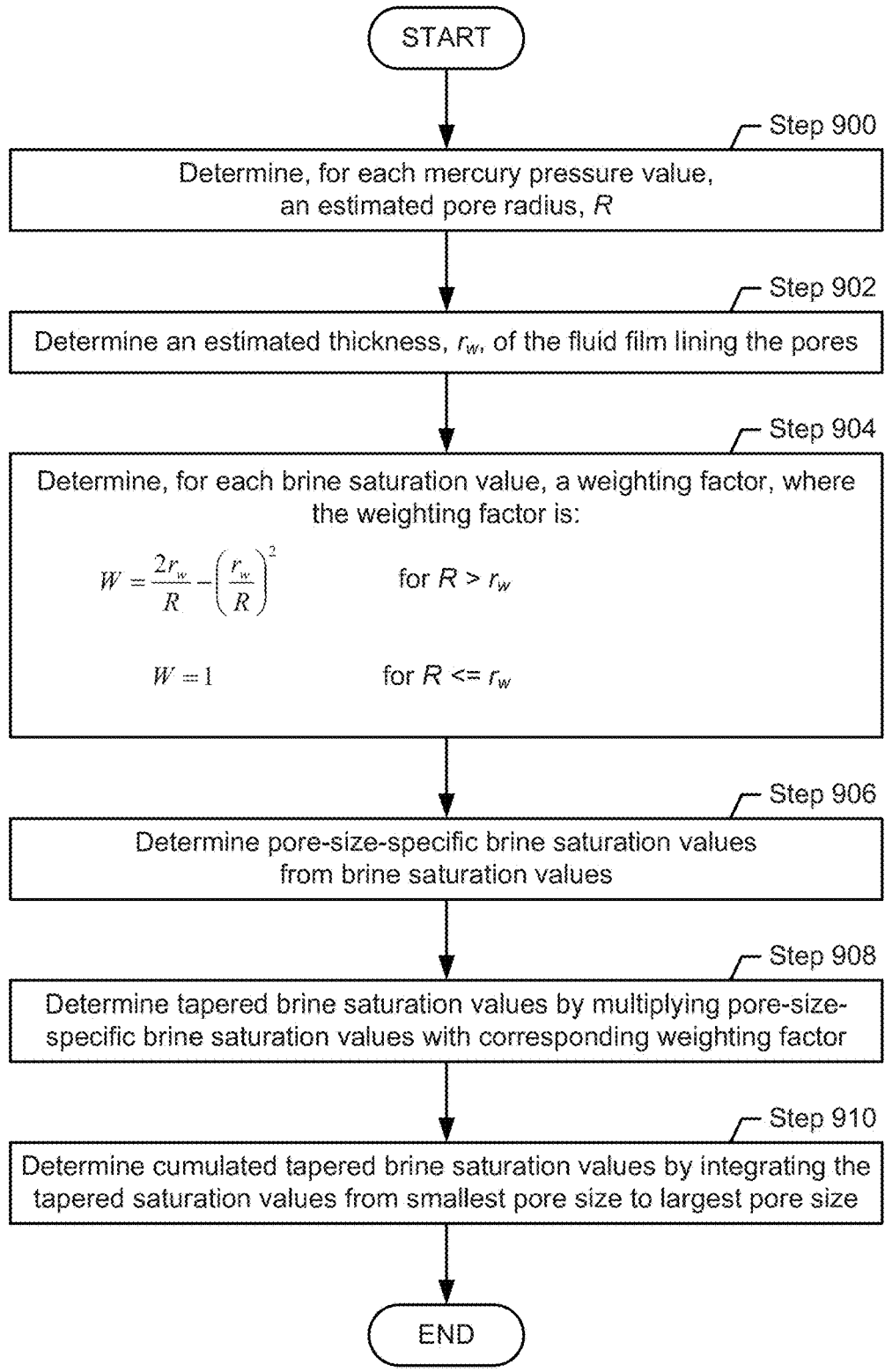

Referring to FIGS. 7-9 a method in accordance with one or more embodiments of the present disclosure is shown. In one or more embodiments, one or more of the elements shown in FIGS. 7-9 may be omitted, repeated, and/or substituted. Accordingly, embodiments of the present disclosure should not be considered limited to the arrangement of elements shown in FIG. 7-9.

As shown in FIG. 7, a reservoir rock sample is obtained in Step 700. The reservoir rock sample may include, for example, a drill core, a mined sample, drill cuttings or fragments, or an outcrop. Additionally, the reservoir rock sample may be obtained from the field at a well site and may be obtained from a well before, during, or after drilling. The reservoir rock sample may be in the form of cuttings or fragments obtained from drilling a borehole, or the rock sample may be a solid core obtained from coring the formation. In addition, in one or more embodiments, the reservoir rock sample may be obtained from a potential hydrocarbon reservoir in a subterranean formation or may be obtained from a hydrocarbon reservoir already in production.

In Step 702, in accordance with one or more embodiments of the present disclosure, a capillary pressure curve is obtained for the reservoir rock sample. In one or more embodiments, the capillary pressure curve may be obtained using a mercury injection capillary pressure (MICP) method. The dried reservoir rock sample may be placed in a chamber of a mercury injection apparatus (1100 in FIG. 10). The reservoir rock sample may be evacuated, and subsequently mercury may be injected into the reservoir rock sample using increasingly higher mercury injection pressures. The pressure required for the injection and the volume of mercury injected into the reservoir rock sample may be recorded. The capillary pressure curve may be obtained by plotting the mercury injection pressure against the volume of mercury injected.

In Step 704, in accordance with one or more embodiments of the present disclosure, the irreducible water saturation, $Sw_{irr}$, is estimated from the mercury injection pressure and mercury saturation values experimentally obtained from the reservoir rock sample in Step 702. The details of Step 704 are described in FIG. 8.

Turning to FIG. 8, in Step 800, in accordance with one or more embodiments of the present disclosure, the mercury injection pressure values, recorded in Step 702, are converted to capillary pressure values appropriate for downhole conditions. Under downhole conditions, there may be, for example an oil-brine contact or a gas-brine contact rather than a mercury-air or mercury-vacuum contact. The mercury injection pressure applied to the reservoir rock sample may be converted to the capillary pressure for downhole conditions according to Equation 3 shown below:

$$P_{cres} = P_{clab}(Hg)\frac{\sigma_{res}\cos(\theta_{res})}{\sigma_{lab}\cos(\theta_{lab})}, \quad (3)$$

where $(\sigma_{res} \cos(\theta_{res}))/(\sigma_{lab} \cos(\theta_{lab}))$ is a scaling factor that converts mercury injection pressure values recorded under laboratory conditions to capillary pressure values under downhole conditions. $P_{c\ res}$ is the capillary pressure under downhole conditions, which may be, for example, oil-brine or gas-brine; $P_{c\ lab}$ is the capillary pressure under laboratory conditions, which may correspond to, for example, the mercury injection pressure applied to the reservoir rock sample in an MICP analysis; $\sigma_{res}$ is the interfacial tension under downhole conditions; and $\sigma_{lab}$ is the interfacial tension under angles laboratory conditions; and $\theta_{res}$ and $\theta_{lab}$ are contact e under downhole and laboratory conditions, respectively. Interfacial tension and contact angle values are well established and may be obtained from tables, such as, for example, Table 1. For example, according to Table 1, a value of 485 dynes/cm may be assumed for $\sigma_{lab}$, and a value of 72 dynes/cm may be assumed for $\sigma_{res}$, for gas-brine downhole conditions. A value of 32 dynes/cm may be assumed for $\sigma_{res}$ for oil-brine downhole conditions, although this value may vary depending on the specifications of the oil. Further, a value of 0 degrees may be assumed for $\theta_{res}$, and a value of 130 degrees may be assumed for $\theta_{lab}$. Alternatively or additionally, interfacial tension and contact angle values may be obtained experimentally.

Further, in Step 800, in accordance with one or more embodiments of the present disclosure, the mercury saturation, obtained experimentally in Step 702, is converted to a water or brine saturation according to Equation 4 shown below:

$$\text{water saturation (\%)} = 100 - \text{mercury saturation (\%)}. \quad (4)$$

In Step 802, in accordance with one or more embodiments of the present disclosure, a set of cumulated tapered brine saturation values is determined from the brine or water saturation values calculated in Step 800. The details of Step 802 are described in FIG. 9.

In Step 804, in accordance with one or more embodiments of the present disclosure, an estimate of the irreducible water saturation, $Sw_{irr}$, is determined. The $Sw_{irr}$ estimate is the cumulated tapered brine saturation value corresponding to the lowest capillary pressure value.

Turning to FIG. 9, in Step 900, in accordance with one or more embodiments of the present disclosure, a reservoir rock pore radius is estimated for each mercury injection pressure value recorded in Step 702. If a mercury injection pressure exceeds the capillary pressure for a pore of a certain radius, the pore may fill with mercury. According to Equation 2, which describes the relationship between capillary pressure and pore size, increasingly higher mercury injection pressures are necessary in order to fill increasingly smaller pores with mercury. Published values of the interfacial tension a and the contact angle θ for mercury in a vacuum or gas environment may be used when solving equation 2 for the pore radius, R, in order to obtain a pore size for each mercury injection pressure applied to the reservoir rock sample in Step 702. For example, σ=485 dynes/cm and θ=130 degrees may be used.

Figure 5:
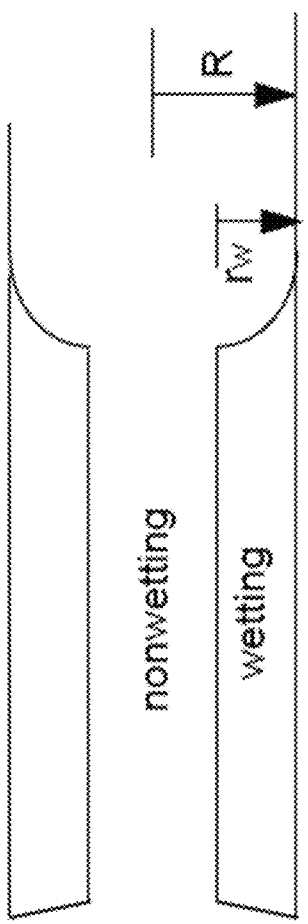
FIG. 5 illustrates a surface film of fluid retained on a pore wall of the reservoir rock in accordance with one or more embodiments of the present disclosure.

In Step 902, in accordance with one or more embodiments of the present disclosure, the thickness of the water or brine film lining the pores of the reservoir rock in accordance with $Sw_{irr}$ model 2 is estimated. The thickness of a fluid film lining a cylindrical pore may be shaped as shown in FIG. 5, and may be determined using Equation 5, derived from the Young Laplace Equation for a narrow tube of circular cross section, as shown below:

$$P_c = \frac{\sigma}{r_w}, \quad (5)$$

where $P_c$ is the capillary pressure; $\sigma$ is the interfacial tension; and $r_w$ is the thickness of the annular cylinder of water or brine forming a film that lines the pore wall at downhole conditions. A cylindrical pore with a fluid film lining the pore wall in accordance with irreducible water saturation model 2 is shown in FIG. 5.

In accordance with one more embodiments of the present disclosure, the thickness of the water film may be estimated experimentally using a nuclear magnetic resonance (NMR) device (1200 in FIG. 10) and NMR methods as described below.

NMR methods may be used to estimate $Sw_{irr}$ based on $T_2$ relaxation time distributions recorded from a reservoir rock sample. Assuming cylindrical pores of radius R, the $T_2$ relaxation time may depend on pore size according to Equation 6 shown below:

$$\frac{1}{T_2} = \rho_2 \frac{S}{V} = \rho_2 \frac{2}{R}, \quad (6)$$

where S is the surface area of the pore; V is the volume of the pore; R is the radius of the pore; and $\rho_2$ is the relaxivity of the fluid solid interface. Accordingly, small pores may result in short $T_2$ relaxation times, and large pores may result in longer $T_2$ relaxation times. $Sw_{irr}$ model 1 predicts that small pores may contain irreducible water, whereas water in larger pores may drain. Accordingly, $Sw_{irr}$ may be predicted from a $T_2$ distribution where $T_2$ values above a $T_2$ threshold, $T_{2\;cutoff}$, i.e. $T_2$ values representing larger pores, are assumed to represent free water, whereas $T_2$ values below the cutoff threshold are assumed to represent irreducible water trapped in small pores. Equation 6, with $T_2=T_{2\;cutoff}$ may therefore provide a threshold pore radius. Pores with a pore radius below the threshold pore radius may be filled with irreducible water, whereas pores with a pore radius above the threshold pore radius may contain free water (irreducible water model 1). A suitable $T_{2\;cutoff}$ value for a particular reservoir rock may be determined experimentally. For example, a $T_2$ cutoff value of 29 ms may be used for sandstone that has been centrifuged to 100 psi air-brine drainage, and a $T_2$ cutoff value of 100 ms may be used for carbonates that have been centrifuged to 100 psi air-brine drainage.

Equations 5 and 6 may be combined to:

$$\frac{r_w}{R} = \frac{\sigma}{2\rho_2 P_c T_{2cutoff}} = \frac{T'}{T_{2cutoff}}, \quad (7)$$

where $T' = \frac{\sigma}{2\rho_2 P_c}$.

Accordingly, $$r_w = \frac{T'}{T_{2cutoff}} R. \quad (8)$$

The ratio, $$\frac{T'}{T_{2cutoff}},$$

is model dependent, and therefore different values may be obtained, depending on whether $Sw_{irr}$ model 1, $Sw_{irr}$ model 2 or other models are used.

Using $Sw_{irr}$ model 1, the factor $$\frac{\sigma}{\rho_2 P_c}$$

is exactly the value of $T_{2\;cutoff}$. Accordingly, $$\frac{T'}{T_{2cutoff}} = 0.5.$$

Figure 6:
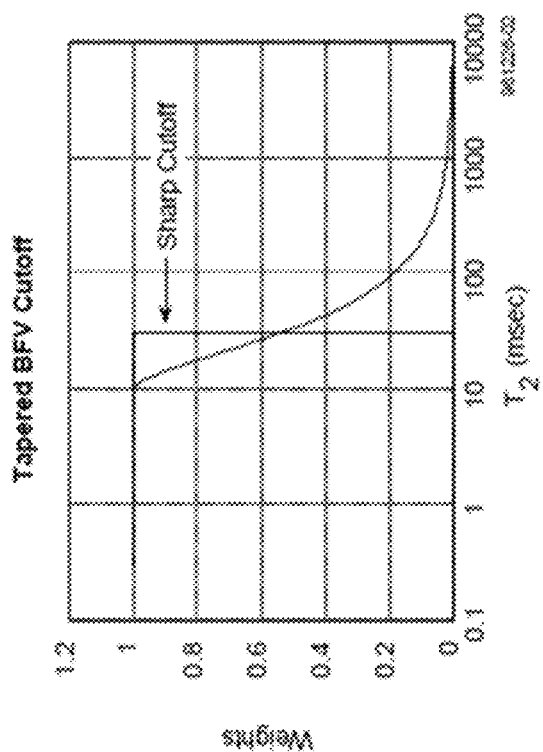
FIG. 6 illustrates sharp and tapered $T_2$ cutoff functions that may be used to obtain irreducible water saturation estimates from nuclear magnetic resonance data in accordance with one or more embodiments of the present disclosure.

$Sw_{irr}$ model 2 may be approximated using a tapered cutoff rather than a sharp cutoff between $T_2$ values counting toward irreducible water and free water. The following equation may be used to implement such a tapered cutoff:

$$BFV = \sum_{T_{2i}=T_{2min}}^{T'} m(T_{2i}) + \sum_{T_{2i}=T'}^{T_{2max}} m(T_{2i})\left(\frac{2T'}{T_{2i}} - \left(\frac{T'}{T_{2i}}\right)^2\right), \quad (9)$$

where BFV is the fluid volume bound in the reservoir rock, i.e. the irreducible water. The function $$\frac{2T'}{T_{2i}} - \left(\frac{T'}{T_{2i}}\right)^2,$$

representing a tapered cutoff, is plotted in FIG. 6, along with the sharp cutoff. T' may now be selected such that, for reservoir rock types where the sharp cutoff is known to provide accurate results, the tapered cutoff provides similar results. Therefore, rather than using the theoretical value $T'=0.5\;T_{2\;cutoff}$, T' may be selected such that the BFV from the tapered and sharp cutoff methods agree for reservoir rock types where the sharp cutoff provides accurate estimates of BFV. Accordingly:

$$\sum_{T_{2i}=T_{2min}}^{T_{2cutoff}} m(T_{2i}) = \sum_{T_{2i}=T_{2min}}^{T'} m(T_{2i}) + \sum_{T_{2i}=T'}^{T_{2max}} m(T_{2i})\left(\frac{2T'}{T_{2i}} - \left(\frac{T'}{T_{2i}}\right)^2\right). \quad (10)$$

Then, $$\sum_{T_{2i}=T'}^{T_{2cutoff}} m(T_{2i}) + \sum_{T_{2i}=T'}^{T_{2max}} m(T_{2i})\left(\frac{2T'}{T_{2i}} - \left(\frac{T'}{T_{2i}}\right)^2\right). \quad (11)$$

Converting the logarithmically spaced sum to an integral, and assuming a flat distribution ($m(T_{2i})=1$ from $T_{2min}$ to $T_{2max}$), $$\int_{T'}^{T_{2cutoff}} d(\ln T_2) = \int_{T'}^{T_{2max}} d(\ln T_2)\left(\frac{2T'}{T_2} - \left(\frac{T'}{T_2}\right)^2\right) \quad (12)$$

gives $\dfrac{T'}{T_{2cutoff}} = \exp(-1.5) = 0.22$.

Another estimate follows the observation that $T_{2cutoff}$ may be coincident with the point on the $T_2$ distribution at which $m(T_{2i})$ is reduced by a factor of two by centrifugation. When this is true, T' can be estimated by $$\frac{1}{2} = \frac{2T'}{T_{2cutoff}} - \left(\frac{T'}{T_{2cutoff}}\right)^2, \quad (13)$$

which gives $\dfrac{T'}{T_{2cutoff}} = 0.29$.

Accordingly, depending on the assumptions made, the ratio, $$\frac{T'}{T_{2cutoff}},$$

may vary between 0.22 and 0.5.

$r_w$ may then be obtained from Equation 8, where R may be 0.29 µm for sandstone, centrifuged to 100 psi air-brine and assuming a surface relaxivity of 5 µm/s, for example. For other types of reservoir rocks, the surface relaxivity constant and the threshold pore radius R may be different, and may be determined experimentally or from tables.

Assuming, for example, $$\frac{T'}{T_{2cutoff}} = 0.25,$$

$r_w = 0.25 \cdot 0.29$ µm $= 0.0725$ µm.

In Step 904, in accordance with one or more embodiments of the present disclosure, weighting factors are determined. A separate weighting factor is determined for each brine saturation value. The weighting factors form a weighting function similar to the tapered cutoff used for NMR based $Sw_{irr}$ determination, as shown in FIG. 6.

Weighting factors analogous to the tapered cutoff used for NMR based $Sw_{irr}$ determination can be derived from Equation 9, as shown below:

$$W_{taper} = \frac{2r_w}{R} - \left(\frac{r_w}{R}\right)^2 \text{ for } R > r_w \quad (14a)$$

$$W_{taper} = 1 \text{ for } R \leq r_w. \quad (14b)$$

In Step 906, in accordance with one or more embodiments of the present disclosure, pore-size-specific brine saturation values are determined from the brine saturation values. The pore-size-specific brine saturations are obtained through numerical differentiation of the brine saturation values determined in Step 800.

In Step 908, in accordance with one or more embodiments of the present disclosure, a tapered brine saturation is determined for each pore-size-specific brine saturation by multiplying the pore-size-specific brine saturation with the corresponding weight, $W_{taper}$.

In Step 910, in accordance with one or more embodiments of the present disclosure, a cumulated tapered brine saturation is determined for each tapered brine saturation by integrating the tapered brine saturations from smallest pore size to largest pore size.

Table 2, shows sample data obtained from a sandstone reservoir rock sample, where the irreducible water saturation, $Sw_{irr}$, is determined for an air-brine interface. The data displayed in Table 2 are intended to provide an example for applying the method of determining an irreducible water saturation, $Sw_{irr}$, as described by FIGS. 7-9. The data are provided for illustrative purposes only. Accordingly, the method described by FIGS. 7-9 is not limited to the data of Table 2.

Columns 1 and 2 contain measurement data obtained from applying the MICP method to the sandstone reservoir rock sample (Step 702). In column 2 of Table 2, the mercury saturation has been converted to brine saturation, Sw (Step 800). Column 4 contains capillary pressure values for an air-brine interface. These capillary pressure values were obtained from the mercury injection pressure values in Column 1 (Step 800). The interfacial tension values used for the conversion were $\sigma_{lab}$=485 dynes/cm and $\sigma_{res}$=72 dynes/cm. Column 3 contains the pore radii corresponding to the mercury injection pressures necessary to overcome the capillary pressures of the reservoir rock pores. These pore radii were derived from the mercury injection pressure values in column 1 (Step 900). The interfacial tension used for the conversion was $\sigma_{lab}$=485 dynes/cm, and the contact angle for mercury, θ, was assumed to be 130 degrees. Column 5 contains an estimate of the thickness of the fluid film lining the pores, $r_w$, based on $Sw_{irr}$ model 2. $r_w$ is derived from nuclear magnetic resonance (NMR) data (Step 902). The ratio T'/$T_2$ was set to 0.25, and a pore radius, R, of 0.29 µm was derived from a surface relaxivity of 5 µm/s for sandstone, centrifuged to 100 psi air-brine drainage. Column 6 contains the pore-size-specific weighting factors obtained from an NMR tapered cutoff function (Step 904). Column 7 contains the pore-size-specific saturation percentages, ΔSw. ΔSw for a specific pore diameter is obtained through numerical differentiation of the brine saturation in Column 2 (Step 906). Column 8 contains the pore-size-specific tapered brine saturations that are determined by multiplying the pore-size-specific ΔSw with the pore-size-specific weighting factor W (Step 908). Column 9 contains the pore-size-specific cumulated tapered brine saturations that are obtained from the pore-size-specific tapered brine saturations through numerical integration from smallest pore radius to largest pore radius (Step 910). The estimate of the irreducible water saturation, $Sw_{irr}$, is the cumulated tapered brine saturation value for the largest pore radius, i.e. the first entry in column 9 (Step 804).

TABLE 2

Calculating $Sw_{irr}$ from MICP data.

| PCHg (psi) | Sw (%) | Radius um | PC-AB (psi) | rw um | w | DSw (%) | W*DSw (%) | SwTaper (%) |
|---|---|---|---|---|---|---|---|---|
| 2.38 | 100 | 44.8 | 0.549654 | 0.073 | 0 | 1.3 | 0 | 23.27 |
| 3.88 | 99 | 27.5 | 0.896074 | 0.073 | 0.01 | 2.4 | 0.01 | 23.27 |
| 6.38 | 96 | 16.7 | 1.473441 | 0.073 | 0.01 | 6.4 | 0.06 | 23.25 |
| 11.4 | 90 | 9.35 | 2.632794 | 0.073 | 0.02 | 7.5 | 0.12 | 23.2 |
| 16.4 | 82 | 6.5 | 3.787529 | 0.073 | 0.02 | 6.3 | 0.14 | 23.08 |
| 21.4 | 76 | 4.98 | 4.942263 | 0.073 | 0.03 | 6.4 | 0.18 | 22.94 |
| 26.4 | 70 | 4.04 | 6.096998 | 0.073 | 0.04 | 4.2 | 0.15 | 22.76 |
| 31.4 | 66 | 3.39 | 7.251732 | 0.073 | 0.04 | 9.2 | 0.39 | 22.61 |
| 45.4 | 56 | 2.35 | 10.48499 | 0.073 | 0.06 | 6.7 | 0.41 | 22.22 |
| 61.4 | 50 | 1.74 | 14.18014 | 0.073 | 0.08 | 3.8 | 0.31 | 21.81 |
| 75.4 | 46 | 1.41 | 17.41339 | 0.073 | 0.1 | 7.6 | 0.76 | 21.5 |
| 111 | 38 | 0.96 | 25.6351 | 0.073 | 0.15 | 4.6 | 0.67 | 20.74 |
| 161 | 34 | 0.662 | 37.18245 | 0.073 | 0.21 | 2.8 | 0.58 | 20.07 |
| 201 | 31 | 0.53 | 46.42032 | 0.073 | 0.25 | 5.3 | 1.35 | 19.49 |
| 301 | 26 | 0.354 | 69.51501 | 0.073 | 0.37 | 3.9 | 1.43 | 18.14 |
| 401 | 22 | 0.266 | 92.6097 | 0.073 | 0.47 | 5.9 | 2.78 | 16.71 |
| 601 | 16 | 0.177 | 138.7991 | 0.073 | 0.65 | 3.4 | 2.21 | 13.93 |
| 801 | 12 | 0.133 | 184.9885 | 0.073 | 0.79 | 2.1 | 1.67 | 11.71 |
| 1000 | 10 | 0.106 | 230.9469 | 0.073 | 0.9 | 1.2 | 1.08 | 10.05 |
| 1200 | 9 | 0.089 | 277.1363 | 0.073 | 0.97 | 0.9 | 0.87 | 8.97 |
| 1500 | 8.1 | 0.071 | 346.4203 | 0.073 | 1 | 0.7 | 0.7 | 8.1 |
| 2000 | 7.4 | 0.053 | 461.8938 | 0.073 | 1 | 7.4 | 7.4 | 7.4 |

Column 1: Hg injection pressure; Column 2: Brine saturation, Sw = (100 – Hg Saturation); Column 3: Pore radius, R; Column 4: Hg injection pressure converted to capillary pressure for an air-brine interface; Column 5: fluid film thickness, $r_w$, Column 6: weighting factor, $W_{taper}$; Colum 7: Pore-size-specific brine saturation, $\Delta$Sw; Column 8: Pore-size-specific tapered brine saturation; Column 9: cumulated tapered brine saturation.

Figure 10:
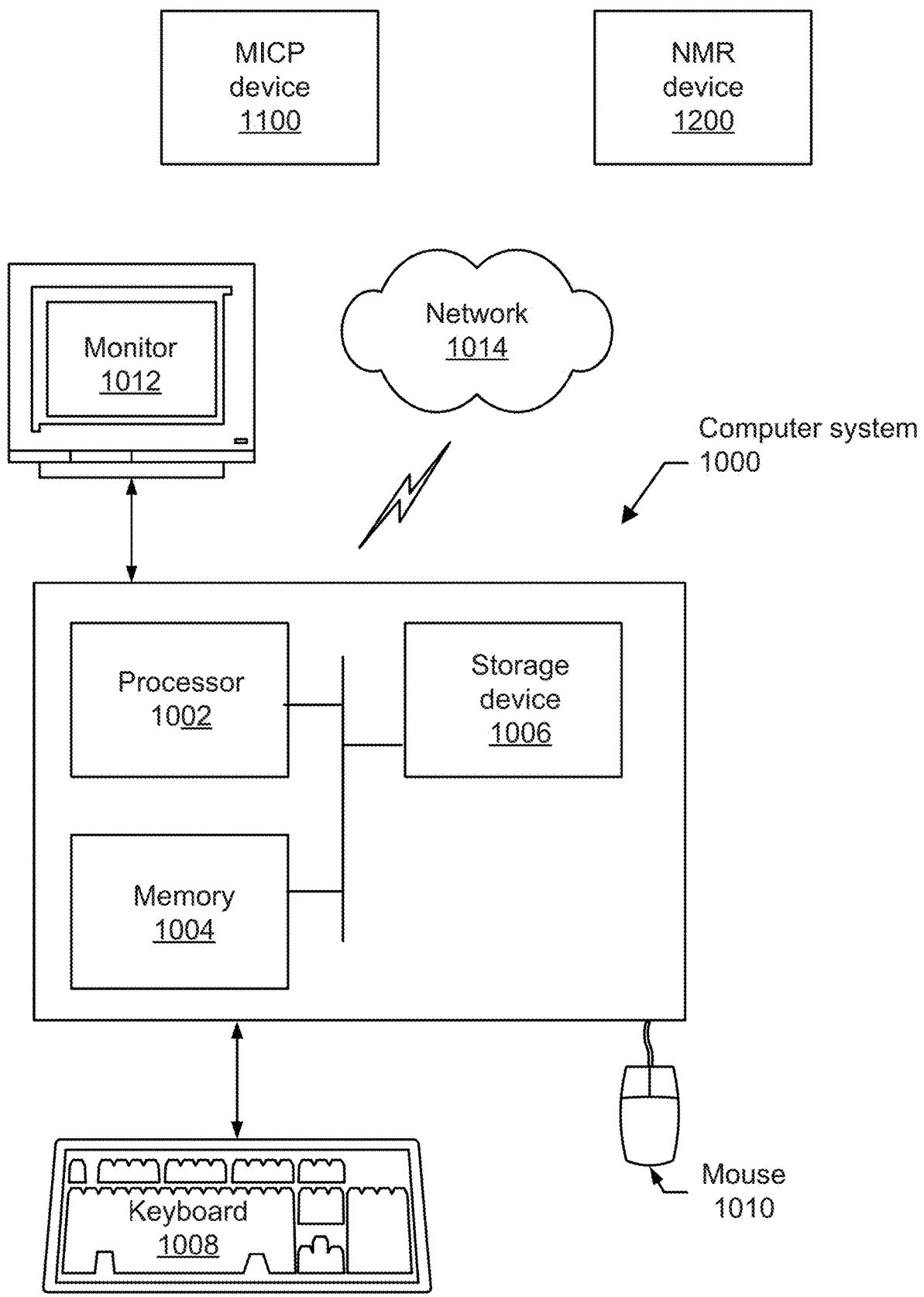
FIG. 10 shows a computer system in accordance with one or more embodiments of the present disclosure.

Embodiments of determining irreducible water saturation in a fluid-storing porous reservoir rock may be implemented on virtually any type of computer regardless of the platform being used. For instance, as shown in FIG. 10, a computer system (1000) includes one or more processor(s) (1002) such as a central processing unit (CPU) or other hardware processor, associated memory (1004) (e.g., random access memory (RAM), cache memory, flash memory, etc.), a storage device (1006) (e.g., a hard disk, an optical drive such as a compact disk drive or digital video disk (DVD) drive, a flash memory stick, etc.), and numerous other elements and functionalities typical of today's computers (not shown). The computer (1000) may also include input means, such as a keyboard (1008), a mouse (1010), or a microphone (not shown). Further, the computer (1000) may include output means, such as a monitor (1012) (e.g., a liquid crystal display LCD, a plasma display, or cathode ray tube (CRT) monitor). The computer system (1000) may be connected to a network (1014) (e.g., a local area network (LAN), a wide area network (WAN) such as the Internet, or any other similar type of network) via a network interface connection (not shown). Those skilled in the art will appreciate that many different types of computer systems exist (e.g., workstation, desktop computer, a laptop computer, a personal media device, a mobile device, such as a cell phone or personal digital assistant, or any other computing system capable of executing computer readable instructions), and the aforementioned input and output means may take other forms, now known or later developed. Generally speaking, the computer system (1000) includes at least the minimal processing, input, and/or output means necessary to practice one or more embodiments.

The computer system (1000) may further interface with an MICP device (1100) that may be used to perform mercury saturation measurements, as described in Step 702. Alternatively, the computer system (1000) may not directly interface with the MICP device (1100). The computer system also may or may not directly interface with an NMR device (1200) that may be used to estimate $T_2$ relaxation times, as described in Step 902.

Further, those skilled in the art will appreciate that one or more elements of the aforementioned computer system (1000) may be located at a remote location and connected to the other elements over a network. Further, one or more embodiments may be implemented on a distributed system having a plurality of nodes, where each portion of the implementation may be located on a different node within the distributed system. In one or more embodiments, the node corresponds to a computer system. Alternatively, the node may correspond to a processor with associated physical memory. The node may alternatively correspond to a processor with shared memory and/or resources. Further, software instructions to perform one or more embodiments may be stored on a computer readable medium such as a compact disc (CD), a diskette, a tape, or any other computer readable storage device.

Embodiments described herein may be advantageous over other laboratory-based $Sw_{irr}$ analysis methods such as, for example, centrifugation or porous plate methods. MICP is a commonly used method for porosity analysis of reservoir rock. In comparison to other methods, it is fast, easy to perform, reliable, and cost effective. Embodiments described in the present disclosure thus may enable rapid and cost effective determination of $Sw_{irr}$ for reservoir rock types based on MICP data, where uncorrected MICP data may not provide accurate estimates of $Sw_{irr}$. Accordingly, embodiments described in the present disclosure enable the use of MICP analysis methods for a variety of reservoir interpretations such as, for example, determining the free water level even if below the total depth of the well, height and location of the transition zone, identification of zones that, at least initially, may produce water-free hydrocarbons, and reassessing zones that have been affected by production causing the free water level to rise.

While several example embodiments have been described in detail above, those skilled in the art, having benefit of this disclosure will appreciate that other embodiments can be devised which do not depart from the scope of this disclosure. Accordingly, all such modification are intended to be included within the scope of this disclosure. Moreover, embodiments described herein may be practiced in the absence of any element that is not specifically disclosed herein.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method for determining irreducible water saturation in a fluid-storing porous reservoir rock sample obtained from an underground fluid reservoir, comprising:
   (a) placing the reservoir rock sample in a mercury injection chamber;
   (b) injecting mercury into the reservoir rock sample in the mercury injection chamber at different mercury injection pressures;
   (c) performing mercury saturation measurements on the reservoir rock sample for the different mercury injection pressures of (b) to obtain mercury saturation values for the different mercury injection pressures; and
   (d) configuring a processor to estimate a value of irreducible water saturation ($Sw_{irr}$) of the reservoir rock sample from the mercury saturation values and the different mercury injection pressures of c) by
      (i) determining a film thickness parameter representing thickness of a thin film of water in the pores of the reservoir rock sample,
      (ii) calculating pore sizes corresponding to the different mercury injection pressures of (b),
      (iii) determining weight factors for the pore sizes of (ii) based upon the film thickness parameter of (i),
      (iv) determining pore-size-specific saturation percentages for the pore sizes of (ii) based upon the mercury saturation values of (c),
      (v) multiplying the weight factor of (iii) and the pore-size-specific saturation percentage of (iv) for each given pore size of (ii) to obtain weighted pore-size-specific saturation percentages for the pore sizes of (ii), and
      (vi) combining a plurality of the weighted pore-size-specific saturation percentages of (v) to obtain the value of irreducible water saturation ($Sw_{irr}$) of the reservoir rock sample.

2. The method of claim 1, wherein the mercury saturation measurements on the reservoir rock sample of (c) comprises applying a mercury injection capillary pressure (MICP) method to the reservoir rock sample.

3. The method of claim 1, wherein the pore sizes of (ii) are determined by:
   converting the mercury saturation values to brine saturation values;
   converting the mercury injection pressures of (b) to capillary pressure values for downhole conditions; and
   using the capillary pressure values for downhole conditions to calculate the pore sizes of (ii).

4. The method of claim 3, wherein the downhole conditions are oil-brine.

5. The method of claim 3, wherein the downhole conditions are gas-brine.

6. The method of claim 3, wherein converting the mercury injection pressures of (b) to capillary pressure values for downhole conditions comprises multiplying each of the mercury injection pressures of (b) with a scaling factor.

7. The method of claim 6, wherein the scaling factor comprises a ratio of an interfacial tension for downhole conditions and an interfacial tension selected from a group consisting of an interfacial tension of mercury in a vacuum environment and an interfacial tension of mercury in an air environment.

8. The method of 3, wherein the pore sizes of (ii) are calculated using the following expression:

$$P_c = \frac{2\sigma \cos\theta}{R},$$

wherein R is a pore size,
wherein $P_c$ is a capillary pressure corresponding to a mercury injection pressure,
wherein $\sigma$ is an interfacial tension of mercury in a vacuum environment, and
wherein $\theta$ is a wetting angle of mercury on a surface.

9. The method of claim 1, wherein the pore-size-specific saturation percentages of (iv) are determined by converting the mercury saturation values of (c) to water or brine saturation values using the following expression:

water or brine saturation=(100−mercury saturation).

10. The method of claim 9, wherein the pore-size-specific saturation values of (iv) are determined by numerical differentiation of the water or brine saturation values.

11. The method of claim 1, wherein the weight factors of (iii) are determined according to a model that distinguishes between small pores and large pores, wherein the small pores are completely filled with irreducible water and the larger pores have walls that retain surface films of irreducible water.

12. The method of 1, wherein the film thickness parameter of (i) is determined from T2 relaxation distributions measured by NMR methods applied to a reservoir rock sample.

13. The method of claim 12, wherein the film thickness parameter of (i) is determined from the following expression:

$$\frac{r_w}{R} = \frac{T'}{T_2},$$

wherein r is the film thickness parameter,
wherein T' is a tapered cut-off value, and
wherein $T_2$ is a relaxation rate.

14. The method of claim 1, wherein the weight factors of (iii) are determined based on a relation between pore size and the film thickness parameter of (i).

15. The method of claim 14, wherein the weight factors of (iii) are determined using the following expression:

$$W = \frac{2r_w}{R} - \left(\frac{r_w}{R}\right)^2, \text{ for } R > r_w, \text{ and}$$

$$W = 1, \text{ for } R \leq r_w,$$

wherein W is a weight factor for a pore size R, and
wherein $r_w$ is the film thickness parameter.

16. The method of claim 1, wherein the combining of (vi) cumulates a plurality of weighted pore-size-specific saturation values to obtain the value of irreducible water saturation ($Sw_{irr}$) of the reservoir rock sample.

17. The method of claim 1, wherein the combining of (vi) integrates a plurality of weighted pore-size-specific saturation values from smallest pore size to largest pore size to obtain the value of irreducible water saturation ($Sw_{irr}$) of the reservoir rock sample.

18. A system for determining irreducible water saturation in a fluid-storing porous reservoir rock sample obtained from an underground fluid reservoir, the system comprising:
    a mercury injection capillary apparatus including a mercury injection sample chamber which is configured to hold the reservoir rock sample in the mercury injection chamber and inject mercury into the reservoir rock sample in the mercury injection chamber at different mercury injection pressures and perform mercury saturation measurements on the reservoir rock sample for the different mercury injection pressures to obtain mercury saturation values for the different mercury injection pressures; and
    a processor configured to estimate a value of irreducible water saturation ($Sw_{irr}$) of the reservoir rock sample from the mercury saturation values measured by the apparatus at the different mercury injection pressures, by
        (i) determining a film thickness parameter representing thickness of a thin film of water in the pores of the reservoir rock sample,
        (ii) calculating pore sizes corresponding to the different mercury injection pressures,
        (iii) determining weight factors for the pore sizes of (ii) based upon the film thickness parameter of (i),
        (iv) determining pore-size-specific saturation percentages for the pore sizes of (ii) based upon the mercury saturation values measured by the apparatus at the different mercury injection pressures,
        (v) multiplying the weight factor of (iii) and the pore-size-specific saturation percentage of (iv) for each given pore size of (ii) to obtain weighted pore-size-specific saturation percentages for the pore sizes of (ii), and
        (vi) combining a plurality of the weighted pore-size-specific saturation percentages of (v) to obtain the value of irreducible water saturation ($Sw_{irr}$) of the reservoir rock sample.

19. The system of claim 18, wherein the pore sizes of (ii) are determined by:
    converting the mercury injection pressures to capillary pressure values for downhole conditions; and
    using the capillary pressure values for downhole conditions to calculate the pore sizes of (ii).

20. The system of claim 18, wherein the pore-size-specific saturation percentages of (iv) are determined by converting the mercury saturation values to water or brine saturation values using the following expression:

water or brine saturation=(100−mercury saturation).

21. The system of claim 18, wherein the weight factors of (iii) are determined according to a model that distinguishes between small pores and large pores, wherein the small pores are completely filled with irreducible water and the larger pores have walls that retain surface films of irreducible water.

22. The system of claim 18, wherein the pore sizes of (ii) are calculated using the following expression:

$$P_c = \frac{2\sigma\cos\theta}{R},$$

wherein R is a pore size,
wherein $P_c$ is a capillary pressure corresponding to a mercury injection pressure,
wherein $\sigma$ is an interfacial tension of mercury in a vacuum environment, and
wherein $\theta$ is a wetting angle of mercury on a surface.

23. The system of 18, wherein the film thickness parameter of (i) is determined from T2 relaxation distributions measured by NMR methods applied to a reservoir rock sample according to the following expression:

$$\frac{r_w}{R} = \frac{T'}{T_2},$$

wherein $r_w$ is the film thickness parameter,
wherein T' is a tapered cut-off value, and
wherein $T_2$ is a relaxation rate.

24. The system of claim 18, wherein the weight factors of (iii) are determined based on a relation between pore size and the film thickness parameter of (i) according to the following expression:

$$W = \frac{2r_w}{R} - \left(\frac{r_w}{R}\right)^2, \text{ for } R > r_w, \text{ and}$$
$$W = 1, \text{ for } R \leq r_w,$$

wherein W is a weight factor for a pore size R, and
wherein $r_w$ is the film thickness parameter.

25. The system of claim 18, wherein the combining of (vi) cumulates a plurality of weighted pore-size-specific saturation values to obtain the value of irreducible water saturation ($Sw_{irr}$) of the reservoir rock sample.

26. The system of claim 18, wherein the combining of (vi) integrates a plurality of weighted pore-size-specific saturation values from smallest pore size to largest pore size to obtain the value of irreducible water saturation ($Sw_{irr}$) of the reservoir rock sample.

* * * * *